United States Patent [19]

Rickwood et al.

[11] Patent Number: 4,913,544
[45] Date of Patent: Apr. 3, 1990

[54] PHOTOCHROMIC ARTICLES

[75] Inventors: Martin Rickwood, Southport; John D. Hepworth, Preston, both of England

[73] Assignee: Pilkington plc, St. Helens, England

[21] Appl. No.: 44,715

[22] Filed: May 1, 1987

[30] Foreign Application Priority Data

May 1, 1986 [GB] United Kingdom ............... 8610709

[51] Int. Cl.$^4$ .................. G02B 27/00; G02B 5/23
[52] U.S. Cl. .................... 351/163; 252/586; 544/59; 544/60; 544/70; 544/71
[58] Field of Search ............ 252/586, 582; 351/163, 351/159; 544/70, 71, 59, 60

[56] References Cited

U.S. PATENT DOCUMENTS

| | | | |
|---|---|---|---|
| 3,231,584 | 1/1966 | Berman | 252/586 |
| 3,485,765 | 12/1969 | Newland | 252/586 |
| 3,501,410 | 3/1970 | Newland | 252/586 |
| 3,508,810 | 7/1967 | Baltzer | 252/586 |
| 3,532,638 | 10/1970 | Otis | 252/586 |
| 3,578,602 | 5/1971 | Ono et al. | 252/586 |
| 4,215,010 | 7/1980 | Hovey et al. | 252/582 |
| 4,287,337 | 9/1981 | Gugliemetti | 252/586 |
| 4,720,356 | 1/1988 | Chu | 252/586 |

FOREIGN PATENT DOCUMENTS

| | | |
|---|---|---|
| 0245020 | 11/1987 | European Pat. Off. |
| 238611 | 8/1986 | German Democratic Rep. |
| 8531295 | 12/1985 | United Kingdom |

OTHER PUBLICATIONS

Techniques of Chemistry, vol. III, Photochromism, Brown, Editor, Wiley Interscience, pp. 48–55, 98–105.
CA 106(20): 157970w, abstract of 238611, E. Germany, Aug. 27, 1986.
Chemical Abstracts Service, Chemical Abstracts, vol. 106, 1987, p. 84, 106: 157970.

Primary Examiner—Mary C. Lee
Assistant Examiner—Catherine S. Scalzo Kilby
Attorney, Agent, or Firm—Burns, Doane, Swecker & Mathis

[57] ABSTRACT

A plastic organic photochromic article, typically a lens such as an ophthalmic lens or a window such as a vehicle roof light, comprisig a plastics host material having a photochromic compound incorporated therein or applied thereto, the article exhibiting the following properties, measured at Air Mass 2 at 25° C.:

(a) an integrated visible transmission in the faded state (B.IVT) ranging from 90 to 25%,
(b) an integrated visible transmission in the darkened state (D.IVT) ranging from 1 to 50%, preferably 4 to 30%,
(c) the rate of darkening of the article when it is exposed to actinic radiation is such that 88% of the darkening range is achieved in 30 seconds or less, i.e. $T_{88} \leq 30$ secs,
(d) the rate of fading of the article from its fully darkened condition is such that more than 60% of the optical density range is recovered in 60 seconds, i.e. % ODG-1 $\geq$ 60%, and
(e) the induced optical density of the article, i.e. the change in the optical density of the article, in moving from the faded state (B.IVT) to the darkened state (D.IVT), is greater than 0.45.

Typically, the photochromic compound is a spiro-oxazine compound of general formula (II),

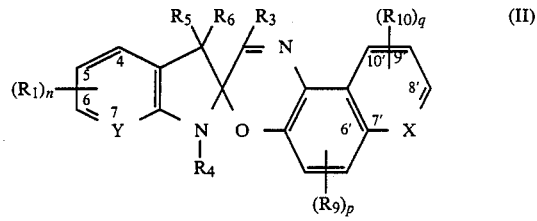

63 Claims, No Drawings

PHOTOCHROMIC ARTICLES

FIELD OF THE INVENTION

The present invention relates to photochromic articles, particularly to articles having organic photochromic material in a plastic matrix, for example photochromic ophthalmic lenses and windows such as vehicle roof lights.

DESCRIPTION OF THE PRIOR ART

Photochromism is a reversible physical phenomenon which is observed with certain classes of chemical compounds which are found to change color when they are exposed to actinic light and which return to their original color when they are removed from the influence of the actinic radiation.

Plastic organic photochromic lenses are known and have been described, for example, in U.S. Pat No. 4215010, European patent application No. 0141407, U.K. patent application No. 2117390 and International patent application No. 85/02619. These patent specifications describe a variety of spiro-oxazine compounds which have been found to be suitable for incorporation into a polymerised host material thereby imparting photochromic properties to the host material.

Plastic organic photochromic windows are known and have been described, for example U.S. Pat. No. 3508810 describes a photochromic window having a photochromic spiro-pyran incorporated into a polyvinyl butyral interlayer between sheets of glass.

SUMMARY OF THE INVENTION

We have now produced plastic organic photochromic articles having a denser coloring in their darkened condition than previously known plastic organic photochromic articles.

Accordingly, the present invention provides a plastic organic photochromic article comprising a plastics host material having a photochromic compound incorporated therein or applied thereto, the article being characterised in that it exhibits the following properties, measured at Air Mass 2 at 25° C.

(a) an integrated visible transmission in the faded state (B.IVT) ranging from 90 to 25%, (b) an integrated visible transmission in the darkened state (D.IVT) ranging from 1 to 50%, preferably 4 to 30%, (c) the rate of darkening of the article when it is exposed to actinic radiation is such that 88% of the darkening range is achieved in 30 seconds or less, i.e. $T_{88} \leq 30$ secs, (d) the rate of fading of the article from its fully darkened condition is such that more than 60% of the optical density range is recovered in 60 seconds, i.e., % $ODG-1 \geq 60\%$, and (e) the induced optical density of the article, i.e. the change in the optical density of the article, in moving from the faded state (B.IVT) to the darkened state (D.IVT), is greater than 0.45.

Throughout this specification the term "integrated visible transmission" or IVT is used to mean the weighted average transmission taking into account the emission from the source $S\lambda$ (in this case Illuminant C (daylight) as defined by the International Commission of Lighting CIE 1964) and the sensitivity of the detector $D\lambda$ (in this case as defined by the CIE 1964 standard colorimetric observer).

i.e. $IVT = \dfrac{\int_{380}^{770} T_\lambda \cdot S_\lambda \cdot D_\lambda \, d\lambda}{\int_{380}^{770} D_\lambda S_\lambda \, d\lambda}$

DETAILED DESCRIPTION OF THE INVENTION

We have found in particular that photochromic articles having such dense coloring can be obtained by applying to or incorporating within a solid transparent plastic host material a photochromic compound represented by the general formula (I):

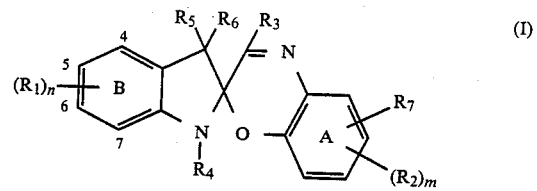

wherein n is an integer of 1 to 4, and m is 1, 2 or 3, each of $R_1$ and $R_2$ independently represents (i) a hydrogen atom or an amine functionality of general formula —NR'R", wherein each of R' and R" independently represents a hydrogen atom or an alkyl, cycloalkyl or phenyl group or a substituted derivative thereof, or an amine functionality which is a cycloheteroalkyl ring or a substituted cycloheteroalkyl ring which ring includes one or more heteroatoms, (ii) a group of formula —R, —OR, —SR, —COR, or —COOR wherein R represents H, alkyl, aryl or heteroaryl, (iii) —Z, —CH$_2$Z, —CHZ$_2$, —CZ$_3$ wherein Z represents halogen, or (iv) —NO$_2$, —CN, —SCN, with the proviso that ring A is always substituted at the 6' position by a group $R_2$ which is an amine-functionality as defined above;

$R_4$ represents —H, alkyl, alkenyl, phenyl, phenylalkyl, mono-, di- or tri-substituted phenyl or alkoxy, each of $R_5$ and $R_6$ independently represents, —H, alkyl, alkenyl, phenyl, phenylalkyl such as benzyl, mono-, di- or tri-substituted phenyl, or $R_5$ and $R_6$ together represent an alicyclic ring including spiro carbons, norbornane, and adamantane, $R_3$ represents a hydrogen atom, or an alkyl, aryl or heteroaryl group, $R_7$ is as defined for $R_1$ and $R_2$ above, or is a ring system fused to ring A, which ring system may incorporate aromatic and/or alicyclic rings, the said ring system optionally carrying one or more substituents $R_8$, the substituent $R_8$ being as defined above for $R_1$ and $R_2$, and Ring B may optionally contain one or more ring nitrogen atoms.

The terms "aromatic" and "alicyclic" used herein should be interpreted to include hetero-aromatic and hetero-alicyclic systems.

Preferably, the photochromic spiro-oxazine compounds of general formula (I) are spiro-oxazines of the formula (II) below:

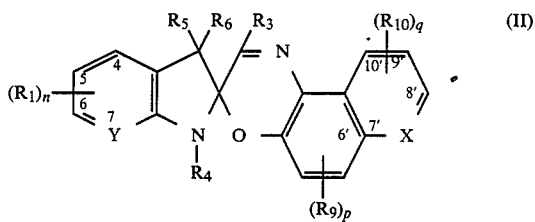

wherein each of $R_1$, $R_9$ and $R_{10}$ independently represents (i) a hydrogen atom or an amine functionality of general formula —NR'R", where each of R' and R" independently represents a hydrogen atom or an alkyl, cycloalkyl or phenyl group or a substituted derivative thereof, or an amine functionality which is a cycloheteroalkyl ring or a substituted cycloheteroalkyl ring, which ring includes one or more heteroatoms, (ii) a group of formula —R, —OR, —SR, —COR, or —COOR wherein R represents H, alkyl, aryl or heteroaryl, (iii) —Z, —CH$_2$Z, —CHZ$_2$, —CZ$_3$ wherein Z represents halogen, or (iv) —NO$_2$, —CN, —SCN: with the proviso that the group (R$_9$)p always includes an amine-functionality as defined immediately above at the 6'-position, n is an integer of 1 to 4, p is 1 or 2, q is 1, 2 or 3, and =X— and =Y— each independently represents

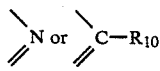

wherein $R_{10}$ is as defined above, and $R_3$, $R_4$, $R_5$ and $R_6$ are as defined above for formula (I).

For convenience, the structural formula (II) depicted above showw the —X= group in the 7'-position of the molecule and the =Y— group in the 7-position, but it should be noted that the —X= group can equally well be located at the 8', 9' or 10'-position of the molecule and the =Y— group can equally well be located at the 4, 5, or 6-position in addition to, or in place of, the depicted position.

In this specification the term "lower alkyl" is intended to mean an alkyl group of from 1 to 8 carbon atoms.

The group $R_3$ is preferably a hydrogen atom.

For the avoidance of doubt, when the substituents $R_1$, $R_2$, $R_9$ or $R_{10}$ represent an amine functionality which is a substituted cycloheteroalkyl ring as defined above, the substituent on the said cycloheteroalkyl ring can take the form of a system of one or more further rings fused to the cycloheteroalkyl ring, which ring system may incorporate saturated and/or unsaturated rings. Typical examples of such a substituted amine-functionality include a tetrahydroisoquinoline substituent of formula

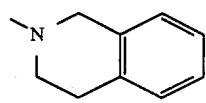

or an indoline substituent of formula

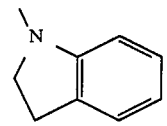

or a hexahydrocarbazole substituent of formula

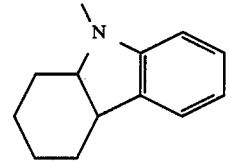

Preferred photochromic materials for incorporation into or application to the plastic host material are compounds of general formula (II) in which n is 1 and $R_1$ is a hydrogen atom, or a 5-alkoxy substituent, preferably 5 methoxy, or a 5-halogen substituent, preferably a 5-chloro substituent; $R_3$ is a hydrogen atom; each of $R_4$, $R_5$ and $R_6$ is an alkyl group, preferably methyl; p is 1 and $R_9$ for example is a 6'-piperidino, 6'-morpholino, 6'-N-methylpiperazino, 6'-N-phenylpiperazino, 6'-tetrahydroisoquinolino, 6'-indolino, 6'-thiomorpholino, 6'-homopiperidino, 6'-(1,2,3,4,4a,9a-hexahydrocarbazolino, or 6'aziridino substituent; q is 1 and $R_{10}$ is a hydrogen atom or an 9'-alkoxy substituent, preferably 9'-methoxy; X is —CH= or —N= located in the 7' position; and Y is —CH= or —N=.

Particularly preferred compounds of general formula (II) are 6'-indolino-1,3,3-trimethylspiro [indoline-2,3'-3H-naphthol[2,1-b][1,4]oxazine] of formula

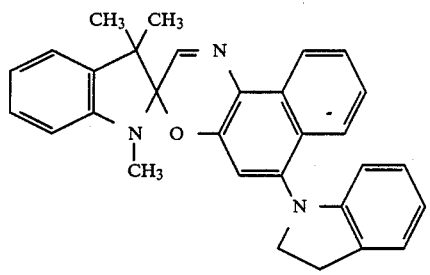

and 5-methoxy-6'-morpholino-1,3,3-trimethylspiro [indoline-2,3'-3H-naphtho[2,1-b][1,4]oxazine] of formula

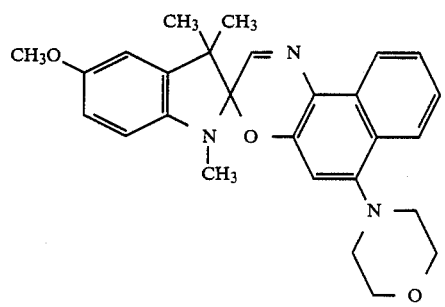

The novel photochromic compounds of formula (II) may be prepared by a general preparative method based on the following reaction scheme:

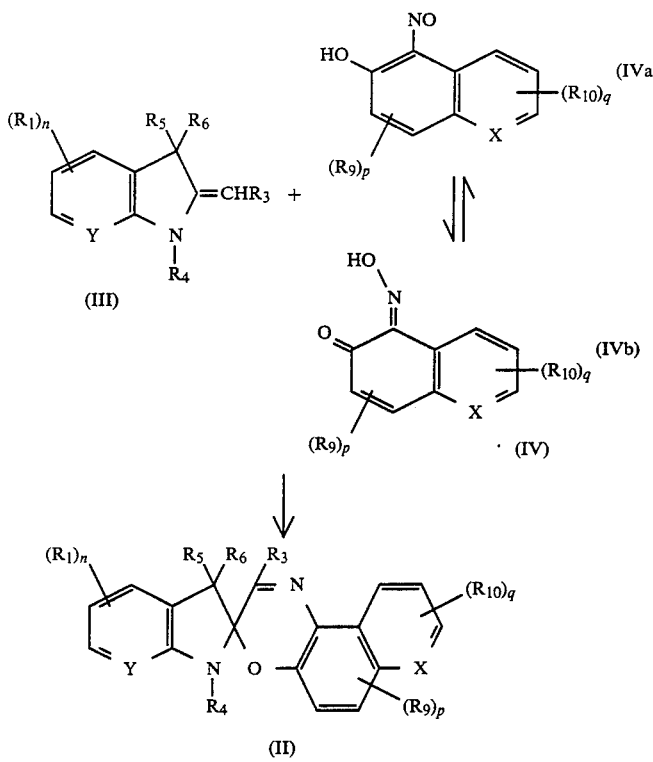

This method is based on the reaction of an α-nitro β-naphthol derivative with a 2-methyleneindole compound such as described in U.S. Pat. No. 3578602.

The compounds of general formula (I) may be prepared by a similar process, using the corresponding starting materials.

In order to prepare the compounds of formula (II), the appropriate nitroso-hydroxy derivative of formula (IV) is reacted with the appropriate indoline of formula (III). Alternatively, an indolenium salt, such as a methiodide, can be used instead of the indoline of formula (III).

The two starting materials are generally reacted together by refluxing in a solvent such as trichloroethylene or toluene. If an indolenium salt is used, a base such as the triethylamine should be present. The desired spiro-oxazine product is separated and purified by conventional techniques such as chromatographic separation and crystallisation.

Examples of suitable plastics host materials are optically clear plastics selected from polymers of polyol(allyl carbonate)-monomers, polyacrylates, poly(alkylacrylates) such as polymethylmethacrylates, cellulose acetate, cellulose triacetate, cellulose acetate propionate, cellulose acetate butyrate, poly(vinyl acetate), poly(vinyl alcohol), polyurethanes, polycarbonates, polyethylene terephthalate, polystyrene, poly(styrene methylmethacrylate) copolymers, poly(styrene acrylonitrile) copolymers, and polyvinylbutyral. Transparent copolymers and blends of the transparent polymers are also suitable as host materials.

Preferably, the host material is an optically clear polymerized organic material such as triethylene glycol dimethacrylate (TEGDM) or a material sold under the trade name CR-39, namely diethylene glycol bis(allyl carbonate).

The photochromic spiro-oxazine compounds of formula (I) may be applied to or incorporated in the plastic host material by any of the conventional methods known in the art, for example by the methods exemplified in European Patent Specification No. 141407. Typically, such methods include dissolving or dispersing the photochromic compound in the host material. The photochromic compound may be dispersed into the host by "imbibition", i.e. diffusion of the photochromic compound into the host material by a suitable transfer mechanism such as immersion, thermal transfer or vapour phase transfer.

In addition, when the plastic host material is one which is formed from a highly reactive polyfunctional monomer the photochromic compounds can be incorporated in the plastic host material by a direct casting process as described in our co-pending U.K. patent application No. 8531295. This direct casting process uses a highly reactive polyfunctional monomer and a low catalyst concentration in order to prevent degradation of the spiro-oxazine compound; the process comprises incorporating into a mixture comprising a highly reactive polyfunctional monomer and 0.01 to 1% by weight, based on the volume of the monomer, of a polymerisation catalyst, 0.05 to 5% by weight, based on the volume of the monomer, of a photochromic spiro-oxazine compound; introducing the resultant polymerisable composition into a mould, and curing the composition to form the shaped synthetic plastic article.

Typically a plastic lens is formed by using a conventional direct casting process in which the polymerisable composition incorporating the photochromic spiro-oxazine compound is introduced into a mould and is then cured by heating. Suitable curing conditions are, for example, heating at a temperature ranging from room temperature to 100° C., generally over a period of about 5 hours. A typically curing schedule is to subject the material to be cured to a temperature beginning at 40°

C. rising up to a temperature within the range 80°-90° C. over a period of about 5 hours.

The highly reactive polyfunctional monomers used in the said direct casting process are preferably methacrylates or acrylates of linear or branched aliphatic or aromatic liquid polyols such as glycols or bisphenols. Examples of specific monomers include ethylene glycol dimethacrylate or diacrylate and the corresponding dimethacrylates or diacrylates of di-, tri- and tetra-ethylene glycol; the dimethacrylates of 1,2-propyleneglycol, of 1,2-dipropylene glycol, of 1,2-tripropylene glycol and of 1,3-butylene glycol; dimethacrylates of propanediol, butanediol, hexanediol and decanediol; trimethylol ethane trimethacrylate, trimethylol propane trimethacrylate, pentaerythritol trimethacrylate, 2,2,4-trimethyl-1,3-pentanediol dimethacrylate and 1,4-cyclohexanediol dimethacrylate.

Mixtures of the reactive polyfunctional monomers may also be used.

The highly reactive polyfunctional monomer or monomers may be used alone or in the presence of other copolymerisable monofunctional monomers which may be added to modify the physical properties - such as impact strength, castability and tintability - of the resultant polymer. The amount of co-monomer which may be added is up to 30% by weight, preferably 5 to 15% by weight, based on the volume of the reactive polyfunctional monomer.

Typical co-monomers are alkyl methacrylates such as cyclohexyl methacrylate, n-butyl methacrylate and lauryl methacrylate, which may be added to improve the impact resistance of the finished lens; ethoxylated bisphenol-A dimethacrylate, which is added to reduce the shrinkage which is found to occur during formation of the moulded article; and hydroxyalkyl methacrylates such as hydroxyethyl methacrylate and hydroxybutyl methacrylate which improve adhesion of the polymers to the mould surface during polymerisation.

Other co-monomer additives include methacrylic acid, aryl methacrylates such as benzyl methacrylate, allyl methacrylate, tetrahydrofurfurylmethacrylate; and polyether monoacrylates or monomethacrylates such as ethoxyethyl methacrylate.

The catalysts used in the said direct casting process are the conventional free-radical polymerisation catalysts used in the art, in particular, organic peroxides such as benzoyl peroxide and peroxydicarbonates such as isopropylperoxydicarbonate. The amount of catalyst used is kept as low as possible, and is from 0.01 to 1% by weight, based on the volume of the monomer.

The amount of the photochromic compound incorporated into the plastic host material is usually of the order of from 0.05% to 5% by weight, based on the volume of the host material. However, the amount of photochromic compound is not critical and can be varied depending upon the method which is used to apply or incorporate the photochromic compound. In particular, when the spiro-oxazine compound is applied to or imbibed into the surface of the article, the amount used will usually be significantly less than 0.05% by weight.

Articles in accordance with the present invention typically exhibit a pale coloration in the faded condition, dependant on the nature of the compound used and a purple to blue color in the darkened condition.

If desired, the color of the article can be modified with conventional water-based dyes or tints. For example, it is possible to make an article which is grey or brown in its faded condition and darkens to a blue/grey coloration when exposed to sunlight.

The present invention is illustrated further by the following Examples.

EXAMPLE 1

Preparation of 6'-indoline-1,3,3-trimethylspiro[indoline-2,3'-3H-naphtho[2,1-b][1,4]oxazine]

1-Nitroso-2-naphthol (17.3 g; 0.1 mol) and indoline (23.8 g; 0.2 mol) were dissolved in trichloroethylene (150 cm$^3$) by heating under reflux. A solution of 1,3,3-trimethyl-2-methyleneindoline (17.3 g; 0.1 mol) in trichloroethylene (100 cm$^3$) was added dropwise over 30 min to the boiling solution. Boiling under reflux was continued for three hours.

The solvent was removed and the oil was adsorbed onto silica and chromatographed in silica using ethyl acetate - light petroleum as eluant. Evaporation of the solvent gave 6'-indolino-1,3,3-trimethylspiro[indoline-2,3'-3H-naphtho[2,1-b][1,4]oxazine], mp 255°–257° C., $^1$H nmr (CDCl$_3$): $\delta$1.36, s, (6H), 3,3-Me$_2$; 2.77, s, (3H), NMe: 3.17, m, (2H), CH$_2$; 3.93, m, (2H), NCH$_2$; 6.93, s, (1H), 5'-H; 7.69, s, (1H), 2'-H.

EXAMPLE 2

Preparation of 1,3,3-trimethyl-6'-piperidinospiro[indoline-2,3'-3H-naphtho[2,1-b][1,4]oxazine]

4-Piperidino-1,2-naphthoquinone (2.41 g, 0.01 mol) was prepared by the same method as is known for the preparation of 4-morpholino-1,2-naphthoquinone. The product was then heated under reflux with hydroxylamine hydrochloride (0.83 g, 0.012 mol) for two hours. The pyridine was removed and the residue dissolved in methylene chloride, washed with water and brine, dried and finally the solvent evaporated to yield an oil. The oil was adsorbed onto silica and chromatographed in silica using methanol/methylene chloride as eluent. Evaporation of the solvent gave 4-piperidino-1,2-naphthoquinone monoxime, m.p. 135°–7° C., [a compound of general formula IV in the tautomeric form having general formula IVb]. This compound was reacted with 1,3,3trimethyl-2-methyleneindoline in boiling trichloroethylene. The solvent was removed and the resulting oil chromatographed in silica to give:

1,3,3-trimethyl-6'-piperindinospiro[indoline-2,3'-3H-naphtho[2,1-b][1,4]oxazine] m.p. 230°–2° C., $^1$H nmr (CDCl$_3$); $\delta$1.35, s, (6H)3,3-Me$_2$; 1.71,br,(6H)(CH$_2$)$_3$; 2.75, s,(3H) NMe; 3.01,br,(4H) N(CH$_2$)$_2$; 6.57,s,(1H)5'-H; 7.61,(1H)2'-H.

EXAMPLE 3–20

Table I below lists a number of photochromic spirooxazine compounds which were made by a process analogous to that described in Example 1 or Example 2; the melting point and partial nmr data obtained for each compound are given in the Table.

TABLE I

| Example | Spiro-oxazine compound and physical data |
|---|---|
| 3 | 9'-Methoxy-1,3,3-trimethyl-6'-piperidinospiro[indoline-2,3-3<u>H</u>-naphtho [2,1-<u>b</u>][1,4]oxazine]mp 180–181° C., $^1$H nmr (CDCl$_3$);, $\delta$1.36, s, (6H), 3,3-Me$_2$; 1.70 brm, (6H), (CH$_2$)$_3$; 2.75, s, (3H), NMe; 2.85, brm, (4H), N(CH$_2$)$_2$; 3.99, s, (3H), OCH$_3$; 6.44, s, (1H), 5'-H; 7.59, s, (1H) 2'-H |

TABLE I-continued

| Example | Spiro-oxazine compound and physical data |
|---|---|
| 4 | 5-Methoxy-1,3,3-trimethyl-6'-piperidinospiro[indoline-2,3'-3H-naphtho[2,1-b][1,4]oxazine] mp 150-2° C., $^1$H nmr (CDCl$_3$); δ1.35, s, (6H), 3,3-Me$_2$; 1.70, br, (6H), (CH$_2$)$_3$; 2.70, s, (3H), NMe; 3.01, br, (4H), N(CH$_2$)$_2$; 3.80, s, (3H), OMe; 6.58, s, (1H), 5'-H; 7.60, s, (1H), 2'-H. |
| 5 | 1,3,3-Trimethyl-6'-morpholinospiro[indoline-2,3'-3H-naphtho[2,1-b][1,4]oxazine] mp 196° C., $^1$H nmr (CDCl$_3$); δ1.36, s, (6H), 3,3-Me$_2$; 2.75, s, (3H), NMe; 3.06, m, (4H), N(CH$_2$)$_2$; 3.96, m, (4H), O(CH$_2$)$_2$; 6.62, s, (1H), 5'-H; 7.47, s, (1H), 2'-H. |
| 6 | 5-Methoxy-1,3,3-trimethyl-6'-morpholinospiro[indoline-2,3'-3H-naphtho[2,1-b][1,4]oxazine] mp 172-3° C., $^1$H nmr (CDCl$_3$); δ1.35, s, (6H), 3,3 Me$_2$; 2.74, s, (3H), N-Me; 3.07, m, (4H), N(CH$_2$)$_2$; 3.81, s, (3H), O-Me; 3.95, m, (4H), O(CH$_2$)$_2$;, 6.64, s, (1H), 5'-H; 7.52, s, 1H 2'-H. |
| 7 | 9'-Methoxy-1,3,3-trimethyl-6'-morpholinospiro[indoline-2,3'-3H-naphtho[2,1-b][1,4]oxazine] mp 197-200° C., $^1$H nmr (CDCl$_3$); δ1.36, s, (6H), 3,3-Me$_2$; 2.76, s, (3H), NMe; 3.04, brm, (4H), N(CH$_2$)$_2$; 3.94, brm, (4H), O(CH$_2$)$_2$; 4.00, s, (3H), OMe; 6.48-8.03, m, (8H) aromatic H. |
| 8 | 5-Chloro-1,3,3-trimethyl-6'-morpholinospiro[indoline-2,3'-3H-naphtho[2,1-b][1,4]oxazine], mp 196° C., $^1$H nmr (CDCl$_3$); δ1.34, s, (6H), 3,3-Me$_2$; 2.73, s, (3H), NMe; 3.07, m, (4H), N(CH$_2$)$_2$; 3.96, m, (4H), O(CH$_2$)$_2$; 6.60, s, (1H), 5'-H; 7.62, s, (1H), 2'-H. |
| 9 | 1,3,3-Trimethyl-6'-thiomorpholinospiro[indoline-2,3'-3H-naphtho[2,1-b][1,4]oxazine], mp 184-5° C., $^1$H nmr (CDCl$_3$); δ1.34, s, (6H), 3,3-Me$_2$; 2.75, s, (3H), NMe; 2.90, m, (4H), N(CH$_2$)$_2$; 3.30, m, (4H), S(CH$_2$)$_2$; 6.61, s, (1H), 5'-H; 7.64, s, (1H), 2'-H. |
| 10 | 1,3,3-Trimethyl-6'-(N-methylpiperazino)spiro[indoline-2,3'-3H-naphtho[2,1-b][1,4]oxazine] mp 203-4° C., $^1$H nmr (CDCl$_3$); δ1.35, s, (6H), 3,3-Me$_2$; 2.41°, s, (3H), NMe; 2.75 m, (3H), NMe and (4H) N(CH$_2$)$_2$; 3.10, m, (4H), N(CH$_2$)$_2$; 6.61, s, (1H) 5'-H; 7.64, s, (1H), 2'-H. |
| 11 | 1,3,3-Trimethyl-6'-(N-phenylpiperazino)spiro[indoline-2,3'-3H-naphtho[2,1-b][1,4]oxazine] mp 207-208° C., $^1$H nmr (CDCl$_3$); δ1.37, s, (6H), 3,3-Me$_2$; 2.77, s, (3H), NMe; 3.35, br m, (8H), (N(CH$_2$)$_2$)$_2$; 6.66, s, (1H), 5'-H; 7.65, s, (1H), 2'-H. |
| 12 | 6'-(1,2,3,4-Tetrahydroisoquinolino)-1,3,3-trimethylspiro[indoline-2,3'-3H-naphtho[2,1-b][1,4]oxazine], mp 188-190° C., $^1$H nmr (CDCl$_3$); δ1.37, s, (6H), 3,3-Me$_2$; 2.77, s, (3H) NMe; 3.26, m, (4H), (CH$_2$)$_2$; 4.25, br. s, (2H), CH$_2$; 6.70, s, (1H), 5'-H; 7.65, s, (1H), 2'-H. |
| 13 | 6'-Homopiperidino-1,3,3-trimethylspiro[indoline-2,3'-3H-naphtho[1,2-b][1,4]oxazine], mp 225° C., $^1$H nmr (CDCl$_3$); δ1.35, s, (6H), 3,3-Me$_2$; 1.80, br. s, (8H), (CH$_2$)$_4$; 2.75, s, (3H), NMe; 3.25, br, (4H), N(CH$_2$)$_2$; 6.63, s, (1H), 5'-H; 7.60, s, (1H), 2'-H. |
| 14 | 6'-Aziridino-1,3,3-trimethylspiro[indoline-2,3'-3H-naphtho[2,1-b][1,4]oxazine] mp 168-170° C., $^1$H nmr (CDCl$_3$); δ1.35, s, (6H), 3,3-Me$_2$; 2.25, br. s, (4H), N(CH$_2$)$_2$; 2.75, s, (3H), NMe; 6.50, s, (1H), 5'-H; 7.62, s, (1H), 2'-H. |
| 15 | 6'-Dimethylamino-1,3,3-trimethylspiro[indoline-2,3'-3H-naphtho[2,1-b][1,4]oxazine] mp 172-173° C., $^1$H nmr (CDCl$_3$); δ1.36, s, (6H), 3,3-Me$_2$; 2.75, (3H), NMe; 2.88, s, (6H), NMe$_2$; 6.59, s, (1H), 5'-H; 7.62, s, (1H), 2'-H. |
| 16 | 6'-Dimethylamino-1,3,3-trimethylspiro[indoline-2,3'-3H-benzo[1,4]oxazine], mp 138-9° C., $^1$H nmr (CDCl$_3$); δ1.30, s, (3H), 3-Me; 1.35, s, (3H), 3-Me; 2.76, s, (3H), NMe; 2.92, s, (6H), NMe$_2$. |
| 17 | 6'-Diethylamino-1,3,3-trimethylspiro[indoline-2,3'-3H-benzo[1,4]oxazine], mp 143-5° C., $^1$H nmr (CDCl$_3$); δ1.12, t, (6H), (CH$_3$)$_2$; 1.28, s, (3H), 3-Me; 1.35, s, (3H), 3-Me; 2.76, s, (3H), NMe; 3.29, q, (4H), N(CH$_2$)$_2$. |
| 18 | 6'-Indolino-1,3,3-trimethylspiro[indoline-2,3'-3H-pyrido[3,2-f][1,4]benzooxazine], mp 231-3° C., $^1$H nmr (CDCl$_3$); δ1.36, s, (6H), 3,3-Me$_2$; 2.78, s, (3H), NMe; 3.20, m, (2H), CH$_2$; 4.23, m, (2H), NCH$_2$; 7.64, s, (1H), 2'-H. |
| 19 | 1,3,3-Trimethyl-6'-piperidinospiro[7-azaindoline-2,3'-3H-naphtho [2,1-b][1,4]oxazine], mp 211° C., $^1$H nmr (CDCl$_3$); δ1.36,s,(6H),3,3-Me$_2$; 1.71,br,(6H),(CH$_2$)$_3$; 2.94,s(3H),NMe; 6.56,s,(1H),5'-H; 7.60,s,(1H),2'-H. |
| 20 | 6'-Indolino-1,3,3-trimethylspiro[7-azaindoline-2,3'-3H-naphtho 2,1-b][1,4]oxazine], mp 192° C., $^1$H nmr(CDCl$_3$); δ1.37,s,(6H)3,3-Me$_2$; 2.98,s,(3H) NMe; 3.25,m,(2H)CH$_2$; 4.00,m,(2H)NCH$_2$; 6.73-8.70,m,(12H)aromatic H; 7.67,s,(1H)2'-H. |

A correlation between the spiro-oxazine compounds of each of Examples 1 to 20 and the general formulae I and II is given in Tables II and III below.

TABLE II

COMPOUNDS OF FORMULA II

| Example No. | -X= | -Y= | R$_1$ | n | R$_3$ | R$_4$ | R$_5$ | R$_6$ | R$_9$ | p | R$_{10}$ | q |
|---|---|---|---|---|---|---|---|---|---|---|---|---|
| 1 | 7'-C= | 7-C= | H | 1 | H | CH$_3$ | CH$_3$ | CH$_3$ | 6'-indolino | 1 | H | 1 |
| 2 | 7'-C= | 7-C= | H | 1 | H | CH$_3$ | CH$_3$ | CH$_3$ | 6'-piperidino | 1 | H | 1 |
| 3 | 7'-C= | 7-C= | H | 1 | H | CH$_3$ | CH$_3$ | CH$_3$ | 6'-piperidino | 1 | 9'-CH$_3$O | 1 |
| 4 | 7'-C= | 7-C= | 5-CH$_3$O | 1 | H | CH$_3$ | CH$_3$ | CH$_3$ | 6'-piperidino | 1 | H | 1 |
| 5 | 7'-C= | 7-C= | H | 1 | H | CH$_3$ | CH$_3$ | CH$_3$ | 6'-morpholino | 1 | H | 1 |
| 6 | 7'-C= | 7-C= | 5-CH$_3$O | 1 | H | CH$_3$ | CH$_3$ | CH$_3$ | 6'-morpholino | 1 | H | 1 |
| 7 | 7'-C= | 7-C= | H | 1 | H | CH$_3$ | CH$_3$ | CH$_3$ | 6'-morphlino | 1 | 9'-CH$_3$O | 1 |
| 8 | 7'-C= | 7-C= | 5-Cl | 1 | H | CH$_3$ | CH$_3$ | CH$_3$ | 6'-morpholino | 1 | H | 1 |
| 9 | 7'-C= | 7-C= | H | 1 | H | CH$_3$ | CH$_3$ | CH$_3$ | 6'-thiomorpholino | 1 | H | 1 |
| 10 | 7'-C= | 7-C= | H | 1 | H | CH$_3$ | CH$_3$ | CH$_3$ | 6'-N—methylpiperazino | 1 | H | 1 |
| 11 | 7'-C= | 7-C= | H | 1 | H | CH$_3$ | CH$_3$ | CH$_3$ | 6'-N—phenylpiperazino | 1 | H | 1 |
| 12 | 7'-C= | 7-C= | H | 1 | H | CH$_3$ | CH$_3$ | CH$_3$ | 6'-(1,2,3,4-tetrahydroisoquinolino) | 1 | H | 1 |
| 13 | 7'-C= | 7-C= | H | 1 | H | CH$_3$ | CH$_3$ | CH$_3$ | 6'-homopiperidino | 1 | H | 1 |
| 14 | 7-C= | 7-C= | H | 1 | H | CH$_3$ | CH$_3$ | CH$_3$ | 6'-aziridino | 1 | H | 1 |
| 15 | 7'-C= | 7-C= | H | 1 | H | CH$_3$ | CH$_3$ | CH$_3$ | 6'-dimethylamino | 1 | H | 1 |
| 18 | 7'-N= | 7-C= | H | 1 | H | CH$_3$ | CH$_3$ | CH$_3$ | 6'-indolino | 1 | H | 1 |
| 19 | 7'-C= | 7-N= | H | 1 | H | CH$_3$ | CH$_3$ | CH$_3$ | 6'-piperidino | 1 | H | 1 |
| 20 | 7'-C= | 7-N= | H | 1 | H | CH$_3$ | CH$_3$ | CH$_3$ | 6'-indolino | 1 | H | 1 |

TABLE III

COMPOUNDS OF FORMULA I

| Example No. | R$_1$ | n | R$_3$ | R$_4$ | R$_5$ | R$_6$ | R$_2$ | m | R$_7$ |
|---|---|---|---|---|---|---|---|---|---|
| 16 | H | 1 | H | CH$_3$ | CH$_3$ | CH$_3$ | 6'-dimethylamino | 1 | H |

TABLE III-continued

COMPOUNDS OF FORMULA I

| Example No. | $R_1$ | n | $R_3$ | $R_4$ | $R_5$ | $R_6$ | $R_2$ | m | $R_7$ |
|---|---|---|---|---|---|---|---|---|---|
| 17 | H | 1 | H | $CH_3$ | $CH_3$ | $CH_3$ | 6'-diethylamino | 1 | H |

Some of the spiro-oxazine compounds of Examples 1 to 20 and two other spiro-oxazines (for comparative purposes) were incorporated into a plastic host material to prepare a plastic photochromic lens.

The ophthalmic lenses were made by a conventional direct casting method using a plano lens mould comprising a pair of glass moulds sealed by a flexible gasket at their interface. The mould cavity was filled with a thermosettable-composition consisting of, as monomer, triethyleneglycol dimethacrylate (TEGDM), with 0.1% by weight, (based on the volume of monomer) of benzoyl peroxide, as initiator, and 0.2% by weight (based on the volume of monomer) of a spiro-oxazine compound of formula I or II. The mixture in the mould was cured by heating at a temperature of 75°–95° C. over a period of about four hours.

The results obtained with lenses incorporating each of the spiro-oxazine compounds of Examples 1 to 20 and the two comparative materials are given in Table IV.

The chromophores used in Comparative Examples 1 and 2 were spiro-oxazines from which substituents of amine functionality were absent. The spiro-oxazine of Comparative Example 1 was
9'-methoxy-1,3,3-trimethylspiro[indoline-2,3'-3H-naphtho[2,1-b][1,4]oxazine],
while that of Comparative Example 2 was
1,3,3-trimethylspiro[indoline-2,3'-3H-naphtho[2,1-b][1,4]oxazine].

The results in Table IV include the integrated visible transmission of the lens in the faded or bleached state (abbreviated as B.IVT) and the integrated visible transmission of the lens in the darkened state (abbreviated as D.IVT). These values show for each material the typical visual photochromic range which can be achieved, and show the suitability of the materials for use in sunlenses. The fully darkened state of a lens made in accordance with the present invention is defined as the state reached by a lens at 25° C. after exposure to standard solar simulation conditions at Air Mass 2 to 10 minutes [see Parry Moon J. Franklin Inst 230 (1940) P583–617]. It can be seen from the results in the Table that in general purple coloring compounds show a wider range than blue coloring materials.

The range at $\lambda_{max}$ gives the bleached and darkened transmissions at the point of maximum absorption of the chromophore, and allows the calculation of induced optical density (IOD):

$$IOD = \log_{10}\frac{BT}{DT}$$

The high IOD's of the spiro-oxizanes of the invention ranging from 0.76 to 2.6 demonstrate the very dense coloring of the samples. These results contrast markedly with the values of induced optical density of 0.29 and 0.23 obtained with the chromophores of Comparative Examples 1 and 2.

An indication of the speed of the photochromic response can be obtained by comparing the time required for the lens, in its darkening phase, to cover 88% of its total available transmission rang ($T_{88}$). The Table shows all the compounds of the invention exhibit fast rates of darkening as indicated by $T_{88}$ less than 60 secs, generally less than 30 secs.

Comparison of the speed at which lenses fade from the darkened state is obtained by comparing % ODG -1 values. This gives the percentage of the induced optical density range recovered after one minute's fading. The higher the value of % ODG-1, the faster is the fading rate of the lens. A fast fading rate would be shown by % ODG-1 greater than 50%; the results in the Table indicate that all compounds of the invention exhibit a % ODG-1 value greater than 50%, in general greater than 70%.

We have also found that lenses in accordance with the present invention exhibit good fatigue resistance.

TABLE IV

| SPIRO OXAZINE OF EXAMPLE NO. | 1 | 9 | 13 | 8 | 16 | 17 | 18 |
|---|---|---|---|---|---|---|---|
| COLOR | BLUE | PURPLE | PURPLE | PURPLE | PURPLE | PURPLE | BLUE |
| B.IVT | 86.4 | 81.8 | 48.0 | 77.9 | 92.9 | 89.3 | 53.2 |
| D.IVT | 19.0 | 22.9 | 7.5 | 19.9 | 37.9 | 31.8 | 9.5 |
| RANGE AT $\lambda$MAX | 77/3 | 70/3 | 31/1 | 70/4.5 | 88/18 | 86/10 | 49.5/1.0 |
| IOD | 1.41 | 1.37 | 1.49 | 1.19 | 0.69 | 0.93 | 1.69 |
| $T_{88}$ (sec) | 3 | 6 | 48 | 15 | 12 | 15 | 9 |
| % ODG-1 | 69 | 62 | 60 | 73 | 75 | 65 | 79 |

| SPIRO OXAZINE OF EXAMPLE NO. | 2 | 5 | 10 | 11 | 4 | 15 | 6 | 12 |
|---|---|---|---|---|---|---|---|---|
| COLOR | PURPLE | BLUEISH-PURPLE | PURPLE | PURPLE | BLUE | PURPLE | BLUE | BLUEISH-PURPLE |
| B.IVT | 69.5 | 77.6 | 60.3 | 70.2 | 63.3 | 53.8 | 50.2 | 59.7 |
| D.IVT | 14.3 | 21.4 | 15.1 | 16.3 | 23.5 | 8.9 | 21.7 | 12.3 |
| RANGE AT $\lambda$MAX | 68/6. | 68/6 | 57/2 | 59.5/2.5 | 45/4.5 | 39/0.1 | 54/9.5 | 52/4 |
| IOD | 1.05 | 1.05 | 1.45 | 1.38 | 1.00 | 2.6 | 0.76 | 1.11 |
| $T_{88}$ (sec) | 18 | 10 | 6 | 8 | 15 | 6 | 18 | 6 |
| % ODG-1 | 80 | 75 | 88 | 76 | 69 | 80 | 68 | 71 |

| SPIRO OXAZINE OF EXAMPLE NO. | 3 | 7 | 19 | 20 | EXAMPLE 1 | EXAMPLE 2 |
|---|---|---|---|---|---|---|
| COLOR | PURPLE | PURPLE | PURPLE | BLUE | BLUE | BLUE |
| B.IVT | 57.2 | 53.7 | 71.4 | 73.0 | 90.5 | 98.5 |
| D.IVT | 6.1 | 11.9 | 13.5 | 9.9 | 44.4 | 66.7 |

TABLE IV-continued

| RANGE AT λMAX | 66/3.7 | 61/2.5 | 66.2/2.1 | 77.5/1.8 | 88/45 | 90/52 |
|---|---|---|---|---|---|---|
| IOD | 1.25 | 1.39 | 1.50 | 1.63 | 0.29 | 0.23 |
| T$_{88}$ (sec) | 42 | 13 | 10 | 6 | 30 | 24 |
| % ODG-1 | 75 | 63 | 64 | 75 | 72 | 77 |

EXAMPLES 21 AND 22

Lenses made as described in Example 1 were modified by pretinting with Sola fast tint brown and Sola fast tint grey, respectively, supplied by Yorkshire Chemicals to produce lenses having a brown pretint (Example 21) or a grey pretint (Example 22).

The optical properties of the lenses were as follows:

| Example | 21 | 22 |
|---|---|---|
| PRETINT | BROWN | GREY |
| COLOR | GREY/BROWN | GREY/BLUE |
| B.IVT (%) | 31 | 38 |
| D.IVT (%) | 9 | 9 |
| Range at λmax | 37/2.5 | 44/1.6 |
| IOD | 1.17 | 1.44 |
| T$_{88}$(secs) | 6 | 6 |
| % ODG-1 | 65 | 69 |

From the results above it will be seen that in Example 21 a brown pre-tinted lens shows an IVT range of 31/9 and darkens to a grey brown with no loss in darkening or fading speeds relative to Example 1. Similarly in Example 22 a grey pretinted lens darkens to a blue/grey with a working range of 38/9 and again no loss in darkening and fading speeds relative to Example 1. A wide range of pretints can be obtained by conventional use of any of the commercially available lens dyes.

A spiro-oxazine compound selected from Examples 1 to 20 was incorporated into a plastic host material to prepare a laminated structure, such as could be utilized in a roof light for motor vehicles. A mixture of the sprio-oxazine compounds of Examples 1 and 2 was dissolved in chloroform, together with polyvinylbutyral. The solution was sprayed onto a glass sheet to give a thin, uniform, coating. The sprayed glass sheet was then laminated to a second glass sheet using a polyvinyl butyral sheet as an interlayer and subjected to autoclaving in a conventional manner, the sprayed surface of the first glass sheet being the surface which contacts the polyvinyl butyral sheet.

On exposure to actinic radiation the laminate turned deep blue and there was a corresponding reduction in the light transmitted through the laminate. The edges of the laminate were sealed to prevent undue degradation of the photochromic material in that vicinity.

The optical properties of the roof light were as follows:

| COLOR | PURPLE/BLUE |
|---|---|
| B.IVT | 82 |
| D.IVT | 10.9 |
| RANGE AT λMAX | 82/2.4 |
| IOD | 1.53 |
| T$_{88}$(sec) | 4 |
| % ODG-1 | 95 |

From these results it can be seen that the photochromic roof light exhibited optical properties comparable to the ophthalmic lens prepared using the photochromic materials according to the invention. Those skilled in the art will realize that ophthalmic lenses and vehical roof lights are merely illustrative of the many photochromic articles that can be made with these spiro-oxazines. Architectural windows, vehical windows and filters are just some of the other applications for these materials.

We claim:

1. A plastic organic photochromic article comprising a plastics host material having a photochromic compound incorporated therein or applied thereto, the article exhibiting the following properties, measured at Air Mass 2 at 25° C.:
   (a) an integrated visible transmission in the faded state (B.IVT) ranging from 90 to 25%,
   (b) an integrated visible transmission in the darkened state (D.IVT) ranging from 1 to 50%,
   (c) the rate of darkening of the article when it is exposed to actinic radiation is such that 88% of the darkening range is achieved in 30 seconds or less, i.e., $T_{88} \leq 30$ secs,
   (d) the rate of fading of the article from its fully darkened condition is such that more than 60% of the optical density range is recovered in 60 seconds, i.e., % ODG-1 $\geq 60\%$, and
   (e) the induced optical density of the article, i.e., the change in the optical density of the article, in moving from the faded state (B.IVT) to the darkened state (D.IVT), is greater than 0.45, wherein the photochromic compound incorporated in or applied to the plastics host material is a photochromic compound of the general formula (I):

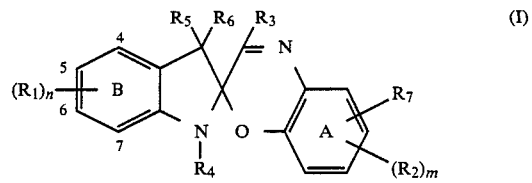

wherein n is an integer of 1 to 4, and m is 1, 2 or 3, each of $R_1$ and $R_2$ independently represents (i) a hydrogen atom or an amine functionality of general formula —NR'R", wherein each of R' and R" independently represents a hydrogen atom or an alkyl, cycloalkyl or phenyl group or a substituted derivative thereof, or an amine functionality which is a cycloheteroalkyl ring or a substituted cycloheteroalkyl ring which ring includes one or more heteroatoms, (ii) a group of formula —R, —OR, —SR, —COR, or —COOR wherein R represents H, alkyl, aryl or heteroaryl, (iii) —Z, —CH$_2$Z, —CHZ$_2$, —CZ$_3$ wherein Z represents a halogen, or (iv) —NO$_2$, —CN, —SCN, with the proviso that ring A is always substituted at the 6' position by a group $R_2$ which is an amine-functionality as defined above;

$R_4$ represents —H, alkyl, alkenyl, phenyl, phenylalkyl, mono-, di- or tri-substituted phenyl or alkoxy, each of $R_5$ and $R_6$ independently represents —H, alkyl, alkenyl, phenyl, phenylalkyl such as benzyl, mono-, di- or tri-substituted phenyl, or $R_5$ and $R_6$ together represent an alicyclic ring including spiro carbons, norbornane, and adamantane, R<sub>3</sub> represents a hydrogen atom, or an alkyl, aryl or heteroaryl group, R<sub>7</sub> is as defined for R<sub>1</sub> and R<sub>2</sub> above, or is a ring system fused to ring A, which ring system may incorporate aromatic and/or alicyclic rings, the said ring system optionally carrying one or more substituents R<sub>8</sub>, the substituent R<sub>8</sub> being as defined above for R<sub>1</sub> and R<sub>2</sub>, and Ring B may optionally contain one or more ring nitrogen atoms.

2. A photochromic article according to claim 1, wherein the photochromic spiro-oxazine compound is 6'-Diethylamino-1,3,3-trimethylspiro[indoline-2,3'-3H-benzo[1,4]oxazine], 3. A photochromic article according to claim 1, wherein the plastics host material is an optically clear plastics selected from polymers of polyol(allyl carbonate)-monomers, polyacrylates, poly(alkylacrylates) such as polymethylmethacrylates, cellulose acetate, cellulose triacetate, cellulose acetate propionate, cellulose acetate butyrate, poly(vinyl acetate), poly(vinyl alcohol), polyurethanes, polycarbonates, polyethyleneterephthalate, polystyrene, poly(styrene-methylmethacrylate) copolymers, poly(styreneacrylonitrile) copolymers, and polyvinylbutyral.

4. A photochromic article according to claim 3, wherein the plastics host material is a polymer or copolymer of diethylene glycol bis (allyl carbonate).

5. A photochromic article according to claim 1, wherein the plastics host material is an optically clear polymer or copolymer of a methacrylate or acrylate of a linear or branched aliphatic or aromatic liquid polyol.

6. A photochromic article according to claim 5, wherein the plastics host material is a polymer or copolymer of triethylene glycol dimethacrylate, ethylene glycol dimethacrylate, 1,3-butyleneglycol dimethacrylate or trimetholpropane trimethacrylate.

7. A photochromic article according to claim 1 which is in the form of an optical lens.

8. A lens according to claim 7 which is an ophthalmic lens.

9. A photochromic article according to claim 1, the said article being incorporated in a window pane.

10. A photochromic article according to claim 9 in the form of a vehicle roof light.

11. A photochromic article according to claim 1, wherein the D.IVT ranges from 4 to 30%.

12. A plastic organic photochromic article comprising a plastics host material having a photochromic compound incorporated therein or applied thereto wherein the photochromic compound is 9'-methoxy-1,3,3-trimethyl-6'-piperidinospiro[indoline-2,3-3H-naphtho[2,1-b][1,4]oxazine].

13. A plastic organic photochromic article comprising a plastics host material having a photochromic compound incorporated therein or applied thereto wherein the photochromic compound is 6'-dimethylamino-1,3,3-trimethylspiro[indoline-2,3'-3H-benzo[1,4]oxazine].

14. A photochromic article according to claim 1, having incorporated therein or applied thereto a photochromic compound of the general formula (II)

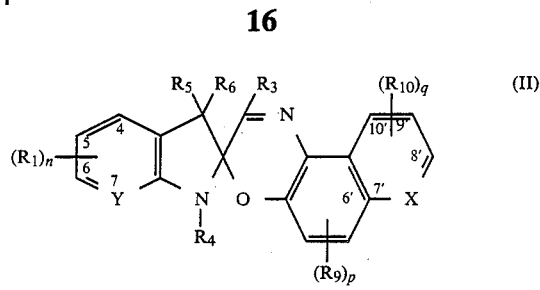

wherein each of R<sub>1</sub>, R<sub>9</sub> and R<sub>10</sub> independently represents (i) a hydrogen atom or an amine functionality of general formula —NR'R", where each of R' and R" independently represents a hydrogen atom or an alkyl, cycloalkyl or phenyl group or a substituted derivative thereof, or an amine functionality which is a cycloheteroalkyl ring or a substituted cycloheteroalkyl ring, which ring includes one or more heteroatoms, (ii) a group of formula —R, —OR, —SR, —COR, or —COOR wherein R represents H, alkyl, aryl or heteroaryl, (iii) —Z, —CH<sub>2</sub>Z, —CHZ<sub>2</sub>, —CZ<sub>3</sub> wherein Z represents halogen, or (iv) —NO<sub>2</sub>, —CN, —SCN: with the proviso that the group (R<sub>9</sub>)p always includes an amine-functionality as defined above at the 6'-position, n is an integer of 1 to 4, p is 1 or 2, q is 1, 2 or 3, and =X— and =Y— each independently represents

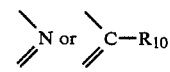

wherein

R<sub>10</sub> is as defined above, and

R<sub>3</sub>, R<sub>4</sub>, R<sub>5</sub> and R<sub>6</sub> are as defined in claim 2 for formula (I).

15. A photochromic article according to claim 14, wherein the photochromic spiro-oxazine compound is 6'-indolino-1,3,3-trimethylspiro[indoline-2,3'-3H-naphtho[2,1-b][1,4]oxazine], 16. A photochromic article according to claim 14, wherein the photochromic spiro-oxazine compound is 1,3,3-Trimethyl-6'-piperidinospiro[indoline-2,3'-3H-naphtho[2,1-b][1,4]oxazine], 17. A photochromic article according to claim 14, wherein the photochromic spiro-oxazine compound is 5-Methoxy-1,3,3-trimethyl-6'-piperidinospiro[indoline-2,3'-3H-naphtho [2,1-b][1,4]oxazine], 18. A photochromic article according to claim 14, wherein the photochromic spiro-oxazine compound is 1,3,3-Trimethyl-6'-morpholinospiro[indoline-2,3'-3H-naphtho [2,1-b][1,4]oxazine], 19. A photochromic article according to claim 14, wherein the photochromic spiro-oxazine compound is 5-Methoxy-1,3,3-trimethyl-6'-morpholinospiro[indoline-2,3'-3H-naphtho [2,1-b][1,4]oxazine], 20. A photochromic article according to claim 14, wherein the photochromic spiro-oxazine compound is 9'-Methoxy-1,3,3-trimethyl-6'-morpholinospiro[indoline-2,3'-3H-naphtho [2,1-b][1,4]oxazine], 21. A photochromic article according to claim 14, wherein the photochromic spiro-oxazine compound is 5-Chloro-1,3,3-trimethyl-6'-morpholinospiro[indoline-2,3'-3H-naphtho [2,1-b][1,4]oxazine], 22. A photochromic article according to claim 14, wherein the photochromic spiro-oxazine compound is 1,3,3-Trimethyl-6'-thiomorpholinospiro[indoline-2,3'-3H-naphtho [2,1-b][1,4]oxazine], 23. A photochromic article according to claim 14, wherein the photochromic spiro-oxazine compound is 1,3,3-Trimethyl-6'-(N-methylpiperazino)spiro[indoline-2,3'-3H-naphtho [2,1-b][1,4]oxazine], 24. A photochromic article according to claim 14, wherein the photochromic spiro-oxazine compound is 1,3,3-Trimethyl-6'-(N-phenylpiperazino)spiro[indoline-2,3'-3H-naphtho [2,1-b][1,4]oxazine], 25. A photochromic article according to claim 14, wherein the photochromic spiro-oxazine compound is 6'-(1,2,3,4-Tetrahydroisoquinolino)-1,3,3-trimethyl-spiro[indoline-2,3'-3H-naphtho [2,1-b][1,4]oxazine], 26. A photochromic article according to claim 14, wherein the photochromic spiro-oxazine compound is 6'-Homopiperidino-1,3,3-trimethylspiro[indoline-2,3'-3H-naphtho [1,2-b][1,4]oxazine], 27. A photochromic article according to claim 14, wherein the photochromic spiro-oxazine compound is 6'-Aziridino-1,3,3-trimethylspiro[indoline-2,3'-3H-naphtho[2,1-b][1,4]oxazine], 28. A photochromic article according to claim 14, wherein the photochromic spiro-oxazine compound is 6'-Dimethylamino-1,3,3-trimethylspiro[indoline-2,3'-3H-naphtho [2,1-b][1,4]oxazine], 29. A photochromic article according to claim 14, wherein the photochromic spiro-oxazine compound is 6'-Indolino-1,3,3-trimethylspiro[indoline-2,3'-3H-pyrido[3,2-f][1,4]benzooxazine], 30. A photochromic article according to claim 14, wherein the photochromic spiro-oxazine compound is 1,3,3-Trimethyl-6'-piperidinospiro[7-azaindoline-2,3'-3H-naphtho [2,1-b][1,4]oxazine], 31. A photochromic article according to claim 14, wherein the photochromic spiro-oxazine compound is 6'-Indolino-1,3,3-trimethylspiro[7-azaindoline-2,3'-3H-naphtho [2,1-b][1,4]oxazine].

32. A photochromic article according to claim 14, wherein the photochromic compound of general formula (II) is one in which n is 1 and $R_1$ is a hydrogen atom, or a 5-alkoxy substituent, or 5-halogen substituent; $R_3$ is a hydrogen atom; each of $R_4$, $R_5$ and $R_6$ is an alkyl group, p is 1 and $R_9$ is a 6'-piperidino, 6'-morpholino, 6'-N-methylpiperazino, 6'-N-phenylpiperazino, 6'-tetrahydroisoquinolino, 6'-indolino, 6'-thiomorpholino, 6'-homopiperidino, 6'-(1,2,3,4,4a,9a-hexahydrocarbazolino, or 6' aziridino substituent; q is 1 and $R_{10}$ is a hydrogen atom or an 9'-alkoxy substituent, X is —CH= or —N= located in the 7' position; and Y is —CH= or —N=.

33. A photochromic article according to claim 1, 14 or 32, wherein the amount of spiro-oxazine compound incorporated in the article is 0.05 to 5% by weight, based on the volume of the polymer host material.

34. A photochromic article according to claim 32, wherein $R_1$ is 5-methoxy.

35. A photochromic article according to claim 32, wherein $R_1$ is a 5-chloro substituent.

36. A photochromic article according to claim 32, wherein each of $R_4$, $R_5$ and $R_6$ is methyl.

37. A photochromic article according to claim 32, wherein $R_{10}$ is 9'-methoxy.

38. A photochromic compound of the general formula:

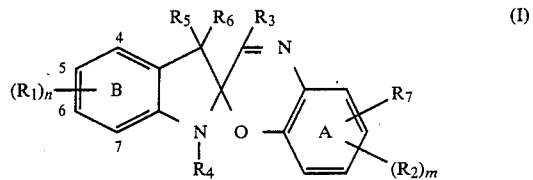

wherein n is an integer of 1 to 4, and m is 1, 2 or 3, each of $R_1$ and $R_2$ independently represents (i) a hydrogen atom or an amine functionality of general formula —NR'R", wherein each of R' and R" independently represents a hydrogen atom or an alkyl, cycloalkyl or phenyl group or a substituted derivative thereof, or an amine functionality which is a cycloheteroalkyl ring or a substituted cycloheteroalkyl ring which ring includes one or more heteroatoms, (ii) a group of formula —R, —OR, —SR, —COR, or —COOR wherein R represents H, alkyl, aryl or heteroaryl, (iii) —Z, —CH$_2$Z, —CHZ$_2$, —CZ$_3$ wherein Z represents halogen, or (iv) —NO$_2$, —CN, —SCN, with the proviso that ring A is always substituted at the 6' position by a group $R_2$ which is an amine-functionality as defined above;

$R_4$ represents —H, alkyl, alkenyl, phenyl, phenylalkyl, mono-, di- or tri-substituted phenyl or alkoxy, each of $R_5$ and $R_6$ independently represents —H, alkyl, alkenyl, phenyl, phenylalkyl such as benzyl, mono-, di- or trisubstituted phenyl, or $R_5$ and $R_6$ together represents an alicyclic ring including spiro carbons, norbornane, and adamantane, $R_3$ represents a hydrogen atom, or an alkyl, aryl or heteroaryl group, $R_7$ is as defined for $R_1$ and $R_2$ above, or is a ring system fused to ring A, which ring system may incorporate aromatic and/or alicyclic rings, the said ring system optionally carrying one or more substituents $R_8$, the substituent $R_8$ being as defined above for $R_1$ and $R_2$, and Ring B may optionally contain one or more ring nitrogen atoms.

39. A photochromic compound according to claim 38, having the general formula (II):

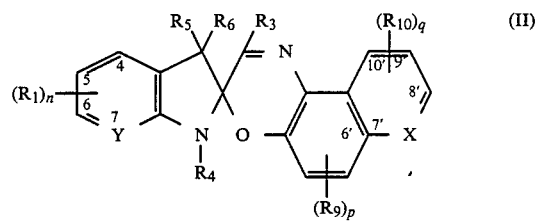

wherein each of $R_1$, $R_9$ and $R_{10}$ independently represents (i) a hydrogen atom or an amine functionality of general formula —NR'R", where each of R' and R" independently represents a hydrogen atom or an alkyl, cycloalkyl or phenyl group or a substituted derivative thereof, or an amine functionality which is a cycloheteroalkyl ring or a substituted cycloheteroalkyl ring, which ring includes one or more heteroatoms, (ii) a group of formula —R, —OR, —SR, —COR, or —COOR wherein R represent H, alkyl, aryl or heteroaryl, (iii) —Z, —CH$_2$Z, —CHZ$_2$, CZ$_3$ wherein Z presents halogen, or (iv) —NO$_2$, —CN, —SCN: with the proviso that the group $(R_9)_p$ always includes an amine-functionality as defined above at the 6'-position, n is an integer of 1 to 4,
p is 1 or 2,
q is 1, 2 or 3, and
=X— and =Y— each independently represents

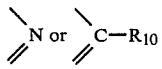

wherein $R_{10}$ is as defined above, and
$R_3$, $R_4$, $R_5$ and $R_6$ are as defined in claim 34 for formula (I).

40. A photochromic compound according to claim 39, wherein the photochromic compound is 6'-indolino-1,3,3-trimethylspiro[indoline-2,3'-3H-naphtho[2,1-b][1,4]oxazine].

41. A photochromic compound according to claim 39, wherein the photochromic compound is 1,3,3-trimethyl-6'-piperidinospiro[indoline-2,3'-3H-naphtho[2,1-b][1,4]oxazine].

42. A photochromic compound according to claim 39, wherein the photochromic compound is 9'-methoxy-1,3,3-trimethyl-6'-piperidinospiro[indoline-2,3-3H-naphtho[2,1-b][1,4]oxazine].

43. A photochromic compound according to claim 39, wherein the photochromic compound is 5-methoxy-1,3,3-trimethyl-6-piperidinospiro[indoline-2,3-3H-naphtho[2,1-b][1,4]oxazine].

44. A photochromic compound according to claim 39, wherein the photochromic compound is 1,3,3-trimethyl-6'-morpholinospiro[indoline-2,3'-3H-naphtho[2,1-b][1,4]oxazine].

45. A photochromic compound according to claim 39, wherein the photochromic compound is 5-methoxy-1,3,3-trimethyl-6'-morpholinospiro[indoline]2,3'-3H-naphtho[2,1-b][1,4]oxazine].

46. A photochromic compound according to claim 39, wherein the photochromic compound is 9'-methoxy-1,3,3-trimethyl-6'-morpholinospiro[indoline-2,3'-3H-naphtho[2,1-b][1,4]oxazine].

47. A photochromic compound according to claim 39, wherein the photochromic compound is 5-chloro-1,3,3-trimethyl-6'-morpholinospiro[indoline-2,3'-3H-naphtho[2,1-b][1,4]oxazine].

48. A photochromic compound according to claim 39, wherein the photochromic compound is 1,3,3-trimethyl-6'-trimorpholinospiro[indoline-2,3'-3H-naphtho[2,1-b][1,4]oxazine].

49. A photochromic compound according to claim 39, wherein the photochromic compound is 1,3,3-trimethyl-6'-(N-methylpiperazino)spiro[indoline-2,3'-3H-naphtho[2,1-b][1,4]oxazine].

50. A photochromic compound according to claim 39, wherein the photochromic compound is 1,3,3-trimethyl-6'-(N-phenylpiperazino)spiro[indoline-2,3'-3H-naphtho[2,1-b][1,4]oxazine].

51. A photochromic compound according to claim 39, wherein the photochromic compound is 6'-(1,2,3,4-tetrahydroisoquinolino)-1,3,3-trimethylspiro[indoline-2,3'-3H-naphtho[2,1-b][1,4]oxazine].

52. A photochromic compound according to claim 39, wherein the photochromic compound is 6'-homopiperidino-1,3,3-trimethylspiro[indoline-2,3'-3H-naphtho[2,1-b][1,4]oxazine].

53. A photochromic compound according to claim 39, wherein the photochromic compound is 6'-aziridino-1,3,3-trimethylspiro[indoline-2,3'-3H-naphtho[2,1-b][1,4]oxazine].

54. A photochromic compound according to claim 39, wherein the photochromic compound is 6'-dimethylamino-1,3,3-trimethylspiro[indoline-2,3'-3H-naphtho[2,1-b][1,4]oxazine].

55. A photochromic compound according to claim 39, wherein the photochromic compound is 6'-indolino-1,3,3-trimethylspiro[indoline-2,3'-3H-pyrido[3,2-f][1,4]benzooxazine].

56. A photochromic compound according to claim 39, wherein the photochromic compound is 1,3,3-trimethyl-6'-piperidinospiro[7-azaindoline-2,3'-3H-naphtho[2,1-b][1,4]oxazine].

57. A photochromic compound according to claim 39, wherein the photochromic compound is 6'-indolino-1,3,3-trimethylspiro[7-azaindoline-2,3'-3H-naphtho[2,1-b][1,4]oxazine].

58. A photochromic compound according to claim 38, wherein the photochromic compound is 6'-dimethylamino-1,3,3-trimethylspiro[indoline-2,3'-3H-benzo[1,4]oxazine].

59. A photochromic compound according to claim 38, wherein the photochromic compound is 6'-diethylamino-1,3,3-trimethylspiro[indoline-2,3'-3H-benzo[1,4]oxazine].

60. A photochromic compound according to claim 39, wherein in the general formula (II), n is 1 and $R_1$ is a hydrogen atom, or a 5-alkoxy substituent, or a 5-halogen substituent; $R_3$ is a hydrogen atom; each of $R_4$, $R_5$ and $R_6$ is an alkyl group; p is 1 and $R_9$ is a 6'-piperidino, 6'-morpholino, 6'-N-methylpiperazino, 6'-N-phenylpiperazino, 6'-tetrahydroisoquinolino, 6'-indolino, 6'-thiomorpholino, 6'-homopiperidino, 6'-(1,2,3,4,4a,9a-hexahydrocarbazolino), or 6'-aziridino substituent; q is 1 and $R_{10}$ is a hydrogen atom or an 9'-alkoxy substituent; X is —CH= or —N= located in the 7'position; and Y is —CH= or —N=.

61. A photochromic compound according to claim 60, wherein $R_1$ is 5-methoxy.

62. A photochromic compound according to claim 60, wherein $R_1$ is a 5-chloro substituent.

63. A photochromic compound according to claim 60, wherein each of $R_4$, $R_5$ and $R_6$ is methyl.

* * * * *